US011248038B2

(12) United States Patent
Bidwell, III et al.

(10) Patent No.: US 11,248,038 B2
(45) Date of Patent: Feb. 15, 2022

(54) MOLECULAR-SIZE OF ELASTIN-LIKE POLYPEPTIDE DELIVERY SYSTEM FOR THERAPEUTICS MODULATES INTRARENAL DEPOSITION AND BIOAVAILABILITY

(71) Applicant: University of Mississippi Medical Center, Jackson, MS (US)

(72) Inventors: Gene L. Bidwell, III, Brandon, MS (US); Alejandro R. Chade, Brandon, MS (US)

(73) Assignee: University of Mississippi Medical Center, Jackson, MS (US)

( * ) Notice: Subject to any disclaimer, the term of this patent is extended or adjusted under 35 U.S.C. 154(b) by 37 days.

(21) Appl. No.: 16/834,549

(22) Filed: Mar. 30, 2020

(65) Prior Publication Data

US 2020/0317750 A1     Oct. 8, 2020

Related U.S. Application Data

(60) Provisional application No. 62/826,413, filed on Mar. 29, 2019.

(51) Int. Cl.
*A61K 38/00* (2006.01)
*C07K 14/78* (2006.01)
*A61P 13/12* (2006.01)

(52) U.S. Cl.
CPC .............. *C07K 14/78* (2013.01); *A61P 13/12* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 7,527,792 | B1 | 5/2009 | Temsamani et al. |
| 2008/0032400 | A1 | 2/2008 | Her |
| 2010/0022466 | A1 | 1/2010 | Raucher |
| 2010/0119529 | A1 | 5/2010 | Furgeson et al. |
| 2010/0233179 | A1* | 9/2010 | Browning ................. A61P 9/00 424/145.1 |
| 2011/0110866 | A1 | 5/2011 | Chilkoti et al. |
| 2013/0172274 | A1 | 7/2013 | Chilkoti |
| 2014/0323315 | A1 | 10/2014 | Bobrowicz et al. |

FOREIGN PATENT DOCUMENTS

| WO | WO97/10507 A1 | 3/1997 |
|---|---|---|
| WO | WO2014/014613 A3 | 1/2013 |

OTHER PUBLICATIONS

Bidwell, et al., A kidney-selective biopolymer for targeted drug delivery, Am J Physiol Renal Physiol 312: F54-F64, 2017.
Chade, et al., Renal Therapeutic Angiogenesis Using a Bioengineered Polymer-Stabilized Vascular Endothelial Growth Factor Construct, J Am Soc Nephrol 27: 1741-1752, 2016.
Chade, et al., Systemic biopolymer-delivered vascular endothelial growth factor promotes therapeutic angiogenesis in experimental renovascular disease, Kidney International (2018) 93, 842-854.
Pasqualini R, Ruoslahti E (1996) Organ targeting in vivo using phage display peptide libraries, Nature 380:364-6. doi: 10.1038/380364a0.
Chade AR, Keisen S (2010) Renal microvascular disease determines the responses to revascularization in experimental renovascular disease. Circ Cardiovasc Interv 3:376-383.
Chade AR, Keisen S (2012) Reversal of renal dysfunction by targeted administration of VEGF into the stenotic kidney a novel potential therapeutic approach. Am J Physiol Ren Physiol 302:F1342-50.
Iliescu R, Fernandez SR, Keisen S, et al. (2010) Role of renal microcirculation in experimental renovascular disease. Nephrol Dial Transplant Off Publ Eur Dial Transpl Assoc—Eur Ren Assoc 25:1079-1087.
Chade, et al., Molecular targeting of renal inflammation using drug delivery technology to inhibit NF-B improves renal recovery in chronic kidney disease, Am J Physiol Renal Physiol 319: F139-F148, 2020.
Mahdi, et al., Utilizing a Kidney-Targeting Peptide to Improve Renal Deposition of a Pro-Angiogenic Protein Biopolymer, Pharmaceutics 2019, 11, 542, pp. 1-21.
Engel, et al., Targeted VEGF (Vascular Endothelial Growth Factor) Therapy Induces Long-Term Renal Recovery in Chronic Kidney Disease via Macrophage Polarization, Hypertension, 2019, pp. 1113-1123.
Guise, et al., Biopolymer-delivered vascular endothelial growth factor improves renal outcomes following revascularization, Am J Physiol Renal Physiol 316: F1016-F1025, 2019.
Kuna, et al., Molecular Size Modulates Pharmacokinetics, Biodistribution, and Renal Deposition of the Drug Delivery Biopolymer Elastin-like Polypeptide, Scientific Reports (2018) 8:7923, pp. 1-12.
Logue, et al., Therapeutic angiogenesis by vascular endothelial growth factor supplementation for treatment of renal disease, Curr Opin Nephrol Hypertens 2016, 25:404-409.
Massodi, et al., Evaluation of Cell Penetrating Peptides Fused to Elastin-Like Polypeptide for Drug Delivery; Journal of Controlled Release; 108; 2005; pp. 396-408.
Dreher, et al., Evaluation of an elastin-like polypeptide-doxorubicin conjugate for cancer therapy; Journal of Controlled Release; 91; 2003; pp. 31-43.

(Continued)

*Primary Examiner* — Jeanette M Lieb
(74) *Attorney, Agent, or Firm* — Stites & Harbison PLLC; Sean P. Ritchie

(57) ABSTRACT

A renal cortex targeting elastin-like polypeptide (ELP), a renal medulla and cortex targeting ELP, and a method of treating a renal disorder are provided. The renal cortex targeting ELP includes up to 95 repeat units having the sequence VPGXG (SEQ ID NO: 1), where X in each of the repeat units is any amino acid except proline. The renal medulla and cortex targeting ELP includes at least 95 repeat units of SEQ ID NO: 1, where X in each of the repeat units is any amino acid except proline. The method of treating a renal disorder includes administering an ELP and a therapeutic drug to a subject in need thereof, where the ELP includes up to 671 repeat units of SEQ ID NO: 1 and X in each of the repeat units is any amino acid except proline.

20 Claims, 6 Drawing Sheets

Specification includes a Sequence Listing.

(56) References Cited

OTHER PUBLICATIONS

Meyer, et al., Targeting a genetically engineered elastin-like polypeptide to solid tumors by local hyperthermia; Cancer Research; 61; pp. 1548-1554; Feb. 15, 2001.

Rousselle C, Clair P, Lefauconnier JM, et al. (2000) New advances in the transport of doxorubicin through the blood-brain barrier by a peptide vector-mediated strategy. Mol Pharmacol 57:679-86.

Vives E, Brodin P, Lebleu B (1997) A truncated HIV-1 Tat protein basic domain rapidly translocates through the plasma membrane and accumulates in the cell nucleus J Biol Chem 272:16010-7.

Ritchie J, Green D, Chrysochou C, et al. (2014) High-risk clinical presentations in atherosclerotic renovascular disease: prognosis and response to renal artery revascularization. Am J Kidney Dis Off J Natl Kidney Found 63:186-197. doi: 10.1053/j.ajkd.2013.07.020.

Textor SC, Lerman LO (2014) Reality and renovascular disease: when does renal artery stenosis warrant revascularization? Am J Kidney Dis Off J Natl Kidney Found 63:175-177. doi: 10 1053/j.ajkd.2013.11.004.

Textor SC, Misra S, Oderich GS (2013) Percutaneous revascularization for ischemic nephropathy: the past, present, and future. Kidney Int 83:28-40. doi: 10.1038/ki.2012.363.

Cooper CJ, Murphy TP, Cutlip DE, et al. (2014) Stenting and medical therapy for atherosclerotic renal-artery stenosis. N Engl J Med 370:13-22. doi: 10 1056/NEJMoa1310753.

Chade AR, Kelsen S (2010) Renal microvascular disease determines the responses to revascularization in experimental renovascular disease. Circ Cardiovasc Interv 3:376-383. doi: 10.1161/CIRCINTERVENTIONS.110.951277.

Chade AR, Kelsen S (2012) Reversal of renal dysfunction by targeted administration of VEGF into the stenotic kidney: a novel potential therapeutic approach. Am J Physiol Ren Physiol 302:F1342-50. doi: 10.1152/ajprenal.00674.2011.

Iliescu R, Fernandez SR, Keisen S, et al. (2010) Role of renal microcirculation in experimental renovascular disease. Nephrol Dial Transplant Off Publ Eur Dial Transpl Assoc—Eur Ren Assoc 25:1079-1087. doi: 10.1093/ndt/gfp605.

Chade AR, Zhu X, Lavi R, et al. (2009) Endothelial progenitor cells restore renal function in chronic experimental renovascular disease. Circulation 119:547-557. doi: 10.1161/CIRCULATIONAHA.108.788653.

Textor, et al.; Renal Artery Stenosis: Medical Versus Interventional Therapy; Curr Cardiol Rep (2013) 15:409; pp. 1-7.

Chade, et al.; Renal Therapeutic Angiogenesis Using a Bioengineered Polymer-Stabilized Vascular Endothelial Growth Factor Construct; J Am Soc Nephrol 27; 2015; pp. 1-12.

Stewart, et al.; Renoprotective effects of hepatocyte growth factor in the stenotic kidney; 2013; Am J Physiol Renal Physiol 304: F625-F633.

Bidwell, et al.; Thermally Targeted Delivery of a c-Myc Inhibitory Polypeptide Inhibits Tumor Progression and Extends Survival in a Rat Glioma Model; PLOS One; 2013; vol. 8; Issue 1; pp. 1-12.

Bidwell, et al.; A thermally targeted c-Myc inhibitory polypeptide inhibits breast tumor growth; Cancer Letters 319 (2012) 136-143.

Bidwell, et al.; A kidney-selective biopolymer for targeted drug delivery; 2017; Am J Physiol Renal Physiol 312: F54-F64.

George, et al., A polypeptide drug carrier for maternal delivery and prevention of fetal exposure; 2014; J Drug Target, Early Online: 1-13.

George, et al., Growth factor purification and delivery systems (PADS) for therapeutic angiogenesis; Vascular Cell (2015) 7:1; pp. 1-10.

\* cited by examiner

MOLECULAR-SIZE OF ELASTIN-LIKE POLYPEPTIDE DELIVERY SYSTEM FOR THERAPEUTICS MODULATES INTRARENAL DEPOSITION AND BIOAVAILABILITY

RELATED APPLICATIONS

This application claims the benefit of U.S. Provisional Application Ser. No. 62/826,413, filed Mar. 29, 2019, the entire disclosure of which is incorporated herein by this reference.

GOVERNMENT INTEREST

This invention was made with government support under grant numbers R01HL121527, R01HL095638, and R41DK109737 awarded by the National Institutes of Health (NIH). The government has certain rights in the invention.

SEQUENCE LISTING

The instant application contains a Sequence Listing which has been submitted in ASCII format via EFS-Web and is hereby incorporated by reference in its entirety. The ASCII copy of the Sequence Listing, which was created on Mar. 30, 2020, is named 11637N-181021.txt and is 1.01 kilobytes in size.

TECHNICAL FIELD

The presently-disclosed subject matter generally relates to articles and methods for targeted delivery of therapeutics to the kidney. In particular, certain embodiments of the presently-disclosed subject matter relate to elastin-like polypeptides and methods of use thereof for targeted delivery of therapeutics to the cortical and medullary regions of the kidney.

BACKGROUND

Elastin-like polypeptides (ELPs) are genetically engineered proteins utilized as a delivery system for therapeutics. Modifications of the sequence composition and length can be achieved by recursive directional ligation, and their influence on the polypeptide's $T_t$ have been extensively studied. Additionally, the ELP sequence is easily modified to include therapeutic peptides and proteins (TP). Additionally, small molecule drugs can easily be chemically attached. These ELP fusions confer increased stability to therapeutic peptides and protein cargo, and they can increase solubility and reduce off-target toxicity of small molecule drugs.

The versatility of ELPs has led to their development as drug carriers in many different disease areas. However, careful analysis of how their physical properties, including chain length and hydrodynamic radius, influence their in vivo behavior has not been systematically described. Accordingly, there remains a need for an ELP with physical properties providing predictable in vivo behavior.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a renal cortex targeting elastin-like polypeptide (ELP) including up to 95 repeat units having the sequence VPGXG (SEQ ID NO: 1), wherein X in each of the repeat units is individually selected from the group consisting of any amino acid except proline. In one embodiment, the ELP comprises between 5 and 95 of the repeat units. In another embodiment, the ELP comprises between 31 and 95 of the repeat units. In a further embodiment, the ELP comprises between 63 and 95 of the repeat units. In one embodiment, the ELP comprises a molecular weight of up to 38 kDa. In another embodiment, the ELP comprises a molecular weight of between 13 kDa and 38 kDa. In some embodiments, the repeat units include V:G:A in a 1:4:3 ratio. In some embodiments, the ELP further includes one or more of a therapeutic agent or agents, a drug binding domain, a targeting domain, and a cell penetrating peptide.

Also provided herein, in some embodiments, is a renal medulla and cortex targeting elastin-like polypeptide (ELP) including at least 95 repeat units having the sequence VPGXG (SEQ ID NO: 1), wherein X in each of the repeat units is individually selected from the group consisting of any amino acid except proline. In one embodiment, the ELP comprises between 95 and 671 of the repeat units. In another embodiment, the ELP comprises between 95 and 450 of the repeat units. In a further embodiment, the ELP comprises between 95 and 287 of the repeat units. In one embodiment, the ELP comprises a molecular weight of at least 38 kDa. In another embodiment, the ELP comprises a molecular weight of between 38 kDa and 257 kDa. In some embodiments, the repeat units include V:G:A in a 1:4:3 ratio. In some embodiments, the ELP further includes one or more of a group selected from a therapeutic agent or agents, a drug binding domain, a targeting domain, and a cell penetrating peptide.

Further provided herein, in some embodiments, is a method of treating a renal disorder, the method including administering an elastin-like peptide (ELP) and a therapeutic drug to a subject in need thereof, where the ELP includes up to 671 repeat units having the sequence VPGXG (SEQ ID NO: 1), and X in each of the repeat units is individually selected from the group consisting of any amino acid except proline. In some embodiments, the ELP includes up to 95 of the repeat units. In some embodiments, the ELP includes at least 95 of the repeat units.

Still further provided herein, in some embodiments, is a method of decreasing the clearance of an elastin-like polypeptides ELP from plasma or a tissue, the method comprising increasing the number of repeat units in the ELP.

Further features and advantages of the presently-disclosed subject matter will become evident to those of ordinary skill in the art after a study of the description, figures, and non-limiting examples in this document.

DESCRIPTION OF EXEMPLARY EMBODIMENTS

Figure 1A:
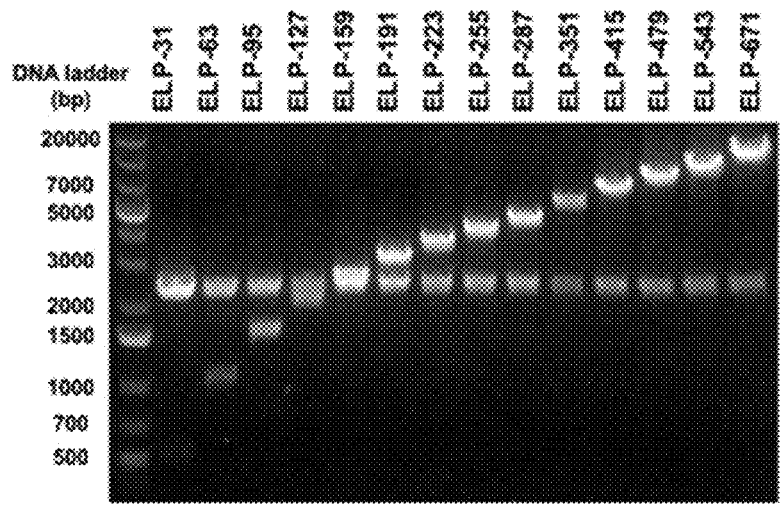
FIGS. 1A-B show images illustrating assessment of ELP expression constructs and protein expression. (A) Evaluation of ELP coding DNA size. (B) Evaluation of expressed peptide molecular weight.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ± 20%, in some embodiments ± 10%, in some embodiments ± 5%, in some embodiments ± 1%, in some embodiments ± 0.5%, and in some embodiments ± 0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is based, at least in part, on the effects of molecular weight on the pharmacokinetics, biodistribution, and renal deposition of elastin-like polypeptides (ELPs), as well as the discovery that different molecular weights provide drug delivery to different intra-renal targets. More specifically, provided herein are specific sized ELP constructs that differentially target the cortical and medullary regions in the kidney (i.e., renal cortex and renal medulla). These ELPs are genetically engineered polypeptides that have a unique physical property called thermal responsiveness. That is, above a characteristic transition temperature, the polypeptide forms aggregates, while below the transition temperature, the aggregates re-dissolve.

Each ELP includes repeated units of a five amino-acid motif having the sequence VPGXG (SEQ ID NO: 1), where each X is individually selected from any amino acid except proline. These individual repeat units may be distributed throughout the ELP in any order, including randomly, in a repeating order, in blocks, or a combination thereof. Additionally or alternatively, the ELP may include any suitable ratio of repeat units having any amino except proline in the X position. For example, in some embodiments, the repeat units of the ELP include V:G:A in a 1:4:3 ratio in the X position.

ELPs with up to about 671 repeat units and/or about 257 kDa accumulate in substantially higher levels in the kidney relative to other organs and exhibit high stability upon incubation in plasma maintained at body temperature. In some embodiments, the ELP half-life and/or hydrodynamic radius increases as the molecular weight of the ELP is increased. As will be appreciated by those skilled in the art, the more repeat units in the ELP, the higher the molecular weight thereof. Surprisingly, ELPs with more repeat units exhibit longer half-life (i.e., are cleared slower from the plasma and tissues) as compared to ELPs with less repeat units. For example, the terminal half-life of ELP compositions with higher molecular weights was 5 to 20-fold longer than smaller ELP proteins of 25 kDa or less. Additionally, the present inventors have unexpectedly and surprisingly found that at certain molecular weights, the ELPs differentially target various regions of the kidney. In particular, the present inventors found that, upon administration, ELPs with up to 95 repeat units and/or a molecular weight of up to 38 kDa accumulate or substantially accumulate solely in the renal cortex (cortical region), while ELPs with more than 95 repeat units and/or a molecular weight of more than 38 kDa accumulate in both the renal cortex and renal medulla (medullary region). Furthermore, the amount of ELP in the renal medulla increased, while the amount of ELP in the renal cortex decreased, with increasing sizes greater than 38 kDa.

Accordingly, in some embodiments, a renal cortex targeting ELP includes up to 95 repeat units, between 5 and 95 repeat units, between 10 and 95 repeat units, between 15 and 95 repeat units, between 20 and 95 repeat units, between 25 and 95 repeat units, between 30 and 95 repeat units, between 31 and 95 repeat units, between 63 and 95 repeat units, or any combination, sub-combination, range, or sub-range thereof. Additionally or alternatively, in some embodiments, the renal cortex targeting ELP includes a molecular weight of up to 38 kDa, between 5 and 38 kDa, between 13 and 38 kDa, between 25 and 38 kDa, or any combination, sub-combination, range, or sub-range thereof.

In other embodiments, a renal medulla targeting ELP includes greater than 95 repeat units, between 95 and 671, between 95 and 600, between 95 and 550, between 95 and 500, between 95 and 450, between 95 and 400, between 95 and 350, between 95 and 300, between 95 and 287 repeat units, or any combination, sub-combination, range, or sub-range thereof. Additionally or alternatively, in some embodiments, the renal medulla targeting ELP includes a molecular weight of greater than 38 kDa, between 38 and 257 kDa, between 38 and 110 kDa, or any combination, sub-combination, range, or sub-range thereof.

Additionally or alternatively, since ELPs are genetically engineered rather than chemically synthesized, the sequence and molecular weight thereof can be precisely controlled. As such, the composition and/or length of the ELP sequence may be modified through know methods, such as, but not limited to, recursive directional ligation. For example, in some embodiments, the composition and/or length of the ELP sequence may be modified to include therapeutic proteins or peptides, targeting proteins or peptides, cell penetrating peptides, reactive sites for chemical attachment of therapeutic agents, or a combination thereof. These modified ELPs form inert and biodegradable macromolecule carriers that have good pharmacokinetic profiles, very low immunogenicity, and can stabilize small proteins, small peptides, and/or small molecule therapeutic agent cargo in systemic circulation. Accordingly, when used as a delivery system for therapeutics, the ELPs disclosed herein provide certain therapeutic advantages to the therapeutic agent(s), such as, but not limited to, comparatively better stability, solubility, bioavailability, half-life, persistence, biological action of the therapeutic proteinaceous component or attached small molecule drug.

In some embodiments, the ELP includes a drug binding domain in place of or in addition to the fused and/or chemically attached therapeutic agent. The drug binding domain facilitates attachment of any suitable known or new small molecule therapeutic agent(s). In some embodiments, the drug binding domain is attached to the ELP carrier via a drug release domain to allow for selective release of the drug under particular environmental conditions or at specific sites within the body. In some embodiments, the drug binding domain improves delivery of the therapeutic agent. For example, the drug binding domain may improve the delivery of therapeutic agents to treat preeclampsia and other pregnancy related disorders, or to treat other diseases that happen to occur during pregnancy such as cancer. Additionally or alternatively, in some embodiments, the ELP coupled therapeutic system includes multiple copies of the therapeutic agent and/or drug binding domain to increase the amount of drug delivered. This may also include the use of two or more different therapeutic agents or different drugs attached to the ELP and/or drug binding domain(s) to achieve combination therapy. Other cases may include both a therapeutic agent/s and a drug binding domain/s to achieve simultaneous delivery of peptide/protein-based therapeutic agents with small molecule drugs.

The ELPs according to one or more of the embodiments disclosed herein facilitate the delivery of a therapeutic drug for treatment of renovascular disease, renal cancer treatment, and other renal related diseases and disorders. Accordingly, also provided herein, in some embodiments, is an ELP delivery system for treatment renal diseases and disorders. In some embodiments, the ELP delivery system includes an ELP according to one or more of the embodiments disclosed herein. In some embodiments, the ELP delivery system includes the ELP and one or more therapeutic drugs. One or more therapeutic drugs attached, encompassed, or otherwise associated with the ELP facilitate the delivery thereof. In some embodiments, the ELP delivery system includes different sized ELPs to deliver one or more therapeutic drugs to different portions of the kidney. For example, in one embodiment, the ELP delivery system includes a therapeutic drug associated with an ELP having up to 95 repeat units for specific delivery to the renal cortex. In another embodiment, the ELP delivery system includes a therapeutic drug associated with an ELP having greater than 95 repeat units for delivery to both the renal cortex and the renal medulla. In yet other embodiments, both therapeutic drugs, one having an ELP up to 95 repeat units and a second having an ELP with greater than 95 repeat units, can be used in combination.

In addition to targeting specific regions of the kidney, the ELPs disclosed herein provide many advantages for drug delivery. For example, ELPs are genetically encoded rather than chemically synthesized. This means the user has absolute control over the ELP sequence and molecular weight (MW), and it allows the addition of targeting peptides and therapeutic peptides. A detailed discussion of targeting peptides and therapeutic peptides is provided in U.S. patent application Ser. No. 16/397,962, which is incorporated by reference herein in its entirety. Additionally, ELP and ELP-fusion proteins can be expressed in *E. coli* and other eukaryotic expression systems allowing large quantities of the molecules to be purified easily because the polypeptide is thermally responsive. Purification of ELP-fusion proteins is achieved by heating a bacterial lysate containing the recombinantly expressed ELP above the polypeptides' transition temperature. This induces ELP aggregation, and it is collected by centrifugation. Repeated centrifugation above and below the transition temperature leads to large quantities of very pure protein. Furthermore, ELPs are large, non-immunogenic macromolecules. Therefore, ELP fusion can stabilize small protein or peptide or small molecule therapeutic agent cargo in systemic circulation, and targeting agents can be used to direct the ELP-fused therapeutics' biodistribution.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

These Examples explore the specific application of ELPs to renal drug delivery, as well as a detailed characterization of how ELP chain length affects the protein's pharmacokinetics and biodistribution, which is critical information when developing ELPs as drug carriers for other disease and conditions applications.

Example 1

Production and Characterization of ELP Proteins with Varying Molecular Weights ELPs were designed with varying coding sequence sizes and denoted by the number of VPGxG (SEQ ID NO: 1) motif repeat units, ranging from 31 repeat units to 671 repeat units (Table 1).

TABLE 1

ELP constructs, their coding sequence size, and predicted protein MW.

| Protein | Number of VPGxG (SEQ ID NO: 1) repeats | Insert size (bp) | Number of amino acid residues | Predicted protein MW (kDa) |
|---|---|---|---|---|
| ELP-31 | 31 | 480 | 170 | 13.0977 |
| ELP-63 | 63 | 960 | 330 | 25.2475 |
| ELP-95 | 95 | 1440 | 490 | 37.3972 |
| ELP-127 | 127 | 1920 | 650 | 49.5469 |
| ELP-159 | 159 | 2400 | 810 | 61.696 |
| ELP-191 | 191 | 2880 | 970 | 73.8463 |
| ELP-223 | 223 | 3360 | 1130 | 85.996 |
| ELP-255 | 255 | 3840 | 1290 | 98.1457 |
| ELP-287 | 287 | 4320 | 1450 | 110.2955 |
| ELP-351 | 351 | 5280 | 1770 | 122.4452 |
| ELP-415 | 415 | 6240 | 2090 | 158.8943 |
| ELP-479 | 479 | 7200 | 2410 | 183.1937 |
| ELP-543 | 543 | 8160 | 2730 | 207.4932 |
| ELP-671 | 671 | 10080 | 3370 | 256.092 |

A library of ELP DNA constructs were generated in which the ratio of amino acids at the X position in the V-P-G-X-G (SEQ ID NO: 1) repeat is V:G:A in a 1:4:3 ratio. All ELP constructs are composed of pentapeptide repeats (SEQ ID NO: 1), denoted ELP-n, where n is the number of pentamer repeats. DNA encoding the ELP-31 sequence in a p-MA-RQ plasmid was custom synthesized (Life Technologies), and all subsequent constructs were synthesized by recursive directional ligation. Each new ELP coding sequence was inserted into the Sfi/site of a pET25b+ expression vector encoding a short N-terminal sequence containing a cysteine residue and short C terminal sequence, resulting in a final coding sequence of MCGPG(VPGxG)nWPGSG (SEQ ID NO: 2), where n is 31 to 671 pentamer repeats. All constructs were confirmed by DNA sequencing (Eurofins Genomics).

For expression and purification, pET25b+ vectors encoding ELP proteins were transformed into E. coli BLR (DE3). All proteins were purified by inverse transition cycling. Briefly, 500 mL of E. coli BLR (DE3) bacterial cultures were grown in TB dry media for 18-20 hours in 2 L flasks. Cells were harvested by centrifugation, lysed by sonication, and nucleic acids were precipitated with polyethyleneimine and removed by centrifugation. NaCl was added to the soluble lysate to a concentration of 200 mg/mL, and the solution was heated at 47° C. until the ELP precipitated. The precipitated ELP was collected by centrifugation, re-dissolved in cold PBS, centrifuged at 4° C. to remove any un-dissolved precipitate, and this heat cycling process was repeated 2 times. ELP was once more precipitated and re-dissolved in a cold solution of 25% ethanol in PBS, centrifuged at 4° C. to remove any un-dissolved precipitate, precipitated again and resuspended in cold PBS. Purity was assessed by SDS-PAGE on a 4-20% Mini-PROTEAN TGX Stain-Free gel.

In FIG. 1A, the synthesized ELP coding DNAs were digested and their size evaluated on an agarose gel. The band at 2.5 kb is the vector backbone, and the band increasing in size is the ELP insert ranging from 480 bp to 10,080 bp corresponding to 31 to 671 ELP repeated units.

Figure 1B:
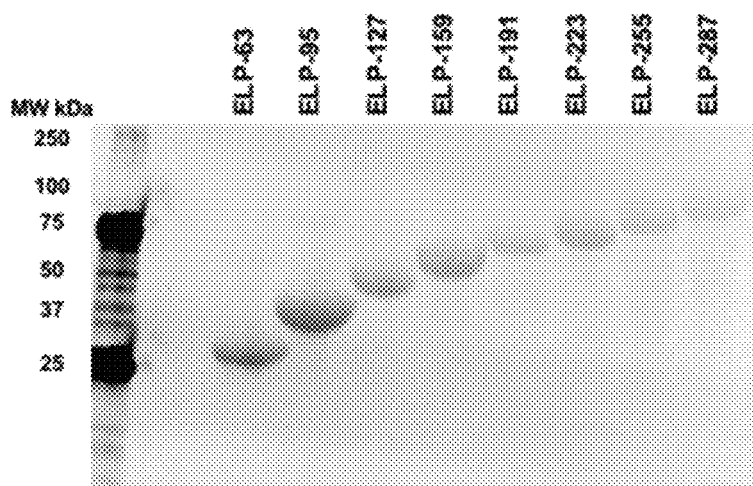

These synthesized DNA constructs were expressed in recombinant expression systems. As shown in FIG. 1B, the recombinant expression system was sufficient for successful production and purification using thermal precipitation of the peptides having sizes between 25 kDa and 110 kDa, corresponding to ELP-63 to ELP-287. ELP protein purity was assessed by SDS-PAGE and visualized using fluorescence imaging of Mini-PROTEAN TGX Stain-Free gels. Proteins were obtained at high purity, and each migrated at the expected molecular weight on an SDS-PAGE gel.

Following purification, proteins ranging from 25 kDa to 110 kDa were characterized in vitro to determine their transition temperature ($T_t$) and hydrodynamic radius (Rh) by turbidity assay and dynamic light scattering, respectively.

The determination of the transition temperature of ELP constructs was performed as follows. ELP samples in phosphate buffered saline were filtered through a Millex-GV hydrophilic Durapore (PVDF) filter with a pore size of 0.22 µm. 10 µM of filtered protein solution was heated at a constant rate of 0.5° C./min in a temperature-controlled multicell holder in a UV-visible spectrophotometer (Cary 100) and the turbidity of the solution was measured as absorbance at 350 nm. The transition temperature ($T_t$) was determined as the temperature at which a maximum was observed in a plot of the first derivative of the turbidity trace using GraphPad Prism version 7.00 for Windows.

The hydrodynamic radius of ELP constructs was measured as follows. 10 µm of filtered (0.22 µm) protein solution was evaluated by dynamic and static light scattering using DynaPro NanoStar (Wyatt Technology) with laser wavelength of 663.53 nm. Batch measurements were performed at a constant temperature of 20° C., the signal acquisition period was set to 5 s, and an averaged result of 10 acquisitions was taken as a measurement. A total of 3 measurements was done. The refractive index increment do/dc for protein was set to 0.185. Data were analyzed using Dynamics software (Wyatt Technology) using a Mw-R model of linear polymers and a static light scattering conformation model of random coil. Radius (nm) and % Mass were expressed as the mean value of the peak of the size distribution from the Regularization Graph using the Coils model in Dynamics.

Figure 2A:
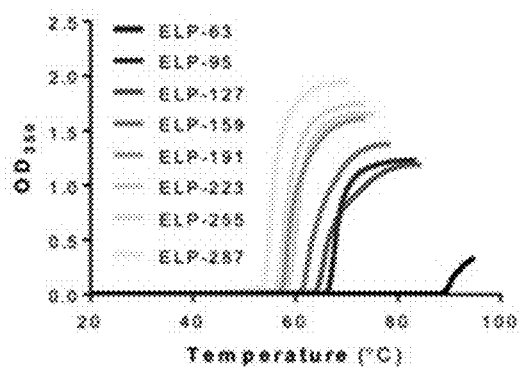
FIGS. 2A-F show graphs illustrating determination of the transition temperature and hydrodynamic radius of ELP constructs. (A) Turbidity profiles of ELP proteins. (B) Transition temperature $T_t$ as a function of ELP molecular weight. (C) Nonlinear regression plot of transition temperature in B. (D) Percent mass of ELP as a function of radius. (E) Radius as a function of ELP molecular weight. (F) Nonlinear regression plot of radius in E.
Figure 2B:
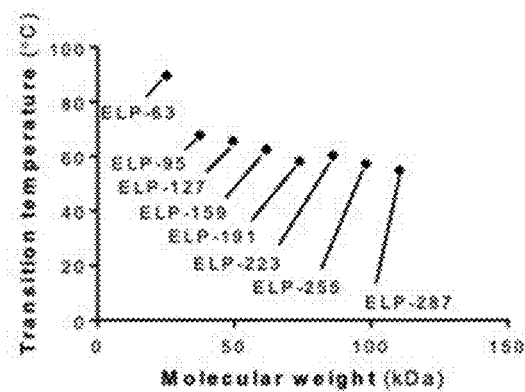
Figure 2C:
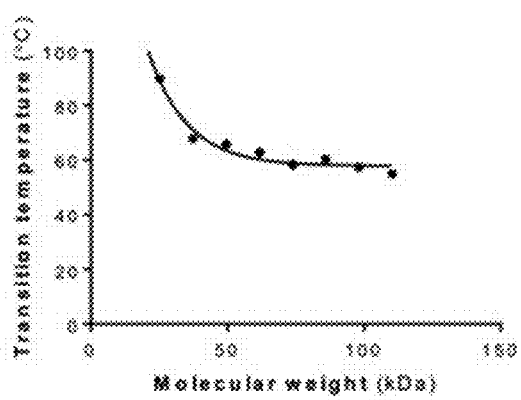
Figure 2D:
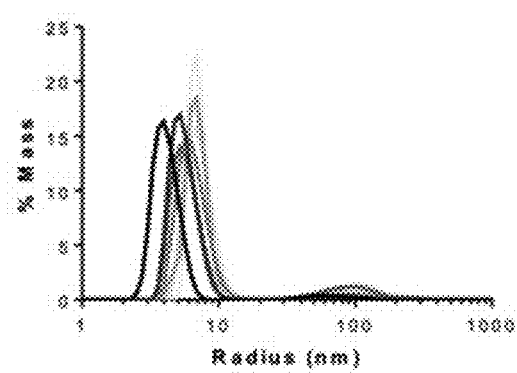
Figure 2E:
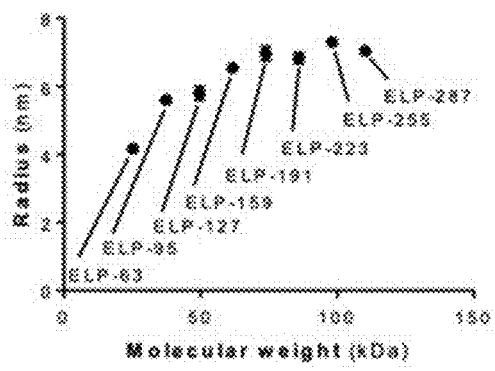
Figure 2F:
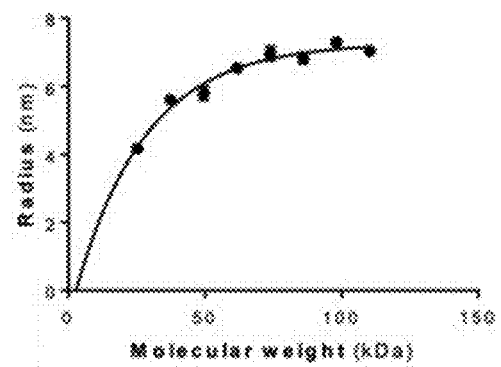

FIG. 2A shows the turbidity profiles (Abs 350 nm) of ELP proteins (10 µM in PBS, 0.22 µm filtered), obtained at a heating rate of 0.5° C./min. In FIGS. 2B-C, the transition temperature $T_t$ is plotted as a function of ELP molecular weight (MW) fit by nonlinear regression using Prism (GraphPad) to a one-phase exponential decay function. $T_t$ was determined as the peak of the first derivative of turbidity. In FIG. 2D-F, the radius, size distribution and estimated relative amount of mass in each peak of species was obtained by dynamic light scattering while the hydrodynamic radius Rh as a function of ELP MW fit was determined by nonlinear regression using Prism (GraphPad) to a one-phase exponential decay function in FIG. 2F.

It was found that with an increase in MW of the ELP protein, the $T_t$ of each protein decreased until it neared an asymptote at 54° C. for the 110 kDa (FIG. 2C). In addition, their radius increased with an increase in MW in the size range from 25 kDa to 110 kDa. Yet, hydrodynamic radius reached an asymptote for the 98 kDa and larger proteins at 7 nm (FIGS. 2D-F). Detailed $T_t$ and hydrodynamic radius data are reported in Table 2.

TABLE 2

Parameters of ELP constructs obtained by turbidity and dynamic light scattering assays.

| Protein | Predicted protein MW (kDa) | Transition temperature (° C.) | Radius (nm) |
| --- | --- | --- | --- |
| ELP-63 | 25.2475 | 89.745 | 4.170 ± 0.056 |
| ELP-95 | 37.3972 | 67.795 | 5.600 ± 0.030 |
| ELP-127 | 49.5469 | 65.775 | 5.800 ± 0.200 |
| ELP-159 | 61.696 | 62.745 | 6.530 ± 0.115 |
| ELP-191 | 73.8463 | 58.370 | 6.967 ± 0.208 |
| ELP-223 | 85.996 | 60.250 | 6.830 ± 0.169 |
| ELP-255 | 98.1457 | 57.295 | 7.300 ± 0.100 |
| ELP-287 | 110.2955 | 54.920 | 7.33 ± 0.058 |

Example 2

Assessment of ELP Stability of Proteins with Varying Molecular Weights

To determine the stability of polypeptides, 50 µM of each fluorescently labeled ELP was incubated in PBS or plasma at 4 or 37° C. for up to 10 days. Fluorophore loss from polypeptides was assessed by measuring fluorescence before and after precipitation of the proteins with 20% TCA. Fluorescence levels after TCA were corrected for dilution and compared to the pre-precipitation fluorescence to calculate the percentage of free dye at each time point. Polypeptide degradation was further assessed by SDS-PAGE on a Bolt 4-12% Bis-Tris Plus gels in reducing conditions for PBS samples and non-reducing conditions for plasma samples. Gels were visualized by direct fluorescence imaging using an IVIS Spectrum (PerkinElmer) and analyzed using Living Image Software. Fluorescence was measured as total radiant efficiency for both the total lane area including the ELP band and the lane area under the ELP band. The percentage of the sample that was degraded was determined by dividing the band intensity below the ELP band by the total band intensity. All calculations were corrected by the signal present at time 0 in order to account for any signal present as lower molecular weight species prior to the incubations. As a control, fluorescently labeled protein was hydrolyzed using a method modified from Zhong, et al. 15 µM of fluorescently labeled protein was resuspended in 500 µl of 25% aqueous trifluoroacetic acid (TFA) solution. 10 µl of protein solution was placed in 1.5 ml polypropylene centrifuge tube, capped and sealed with a Teflon tape. Sample was microwave irradiated for 10 min, followed by vacuum centrifugation (Savant Speed Vac Concentrator) to remove the acid which was repeated until an adequate amount of the protein was hydrolyzed. Hydrolyzed protein was resuspended in $H_2O$, and the sample was prepared for SDS-PAGE analysis.

Each ELP protein was fluorescently labeled on its N-terminal cysteine residue using a maleimide conjugate of rhodamine. Proteins were diluted to 200 µmon in 50 mM $NaH_2PO_4$ pH 7 buffer, and tris-(2-carboxyethyl) phosphine (TCEP) was added to a 10-fold molar excess. Tetramethylrhodamine-5-maleimide (Molecular Probes) was added to a 2-fold molar excess and the reaction was allowed to proceed overnight at 4° C. Unreacted dye was removed by multiple washes with an Amicon 3,000 molecular weight cutoff spin filter (Merck Millipore). Labeling efficiency was assessed by UV-visible spectrophotometry (NanoDrop 2000, Thermo Fisher Scientific, Waltham, Mass.). Removal of unreacted label was confirmed by trichloroacetic acid (TCA) precipitation of the labeled protein and assessing the free fluorophore levels in the supernatant spectrophotometrically.

Figure 3A:
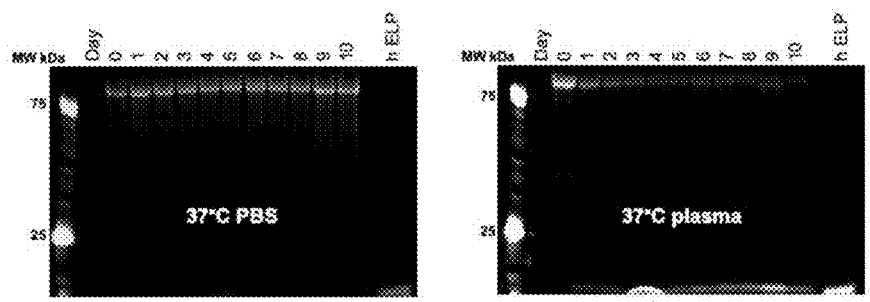
FIGS. 3A-C show images and graphs illustrating the stability of ELP constructs. (A) Representative gels demonstrating stability of 86 kDa ELP in PBS (left) and plasma (right) at 37° C. (B) Degradation of ELPs in PBS (left) and plasma (right) at 4° C. (top) and 37° C. (bottom). (C) Free dye released from fluorescently-labeled ELP in PBS (left) and plasma (right) at 4° C. (top) and 37° C. (bottom).
Figure 3B:
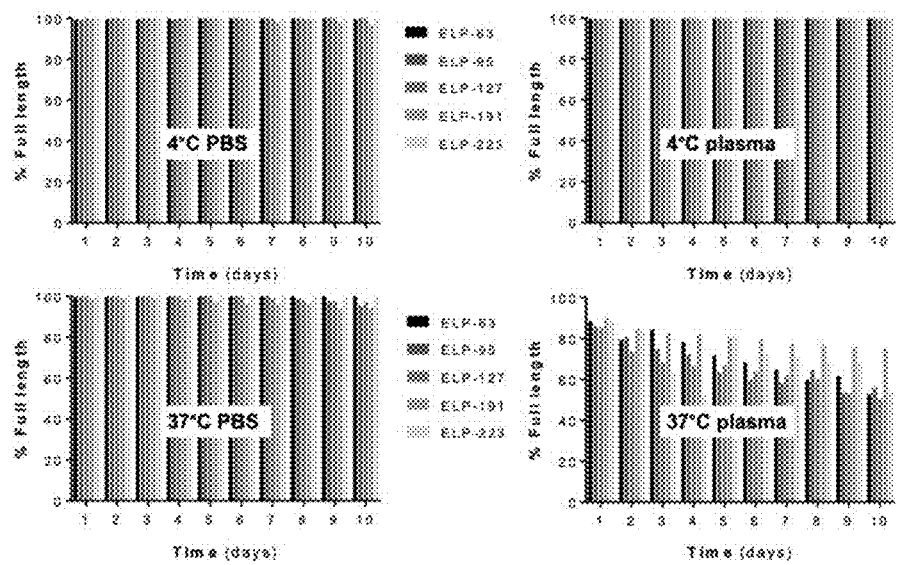

ELP stability was assessed in vitro by determining the percent of fluorescently labeled full length polypeptide present after up to 10 days of incubation in either PBS or plasma at 4 or 37° C., and by determining the percent of dye released from the polypeptide. Five ELP proteins were selected with a range of MW from 25 to 86 kDa. A representative example gel is shown in FIG. 3A of the results from the 86 kDa protein at 37° C. All polypeptides proved to be stable in PBS at both 4 and 37° C., and in plasma at 4° C., with only minimal degradation detected at very late time points (FIG. 3B). The SDS-PAGE gel shown is for ELP-223 (86 kDa) with hydrolyzed ELP (KELP) as a positive control and visualized by direct fluorescence imaging of the fluorescently-labeled ELP.

Some degradation of the polypeptides was observed when incubated in plasma at 37° C. (FIG. 3B, lower right). Polypeptide stability was quantified from the SDS-PAGE analysis for all sizes of ELP proteins. About 80-90% of the proteins were still present as full-length protein on day 1, and each showed a slow degradation over the ten-day time course. On day 10 for ELP-63, ELP-95, ELP-127, ELP-191 and ELP-223, the percent of full length was 53, 56, 51, 75 and 53%, respectively.

Figure 3C:
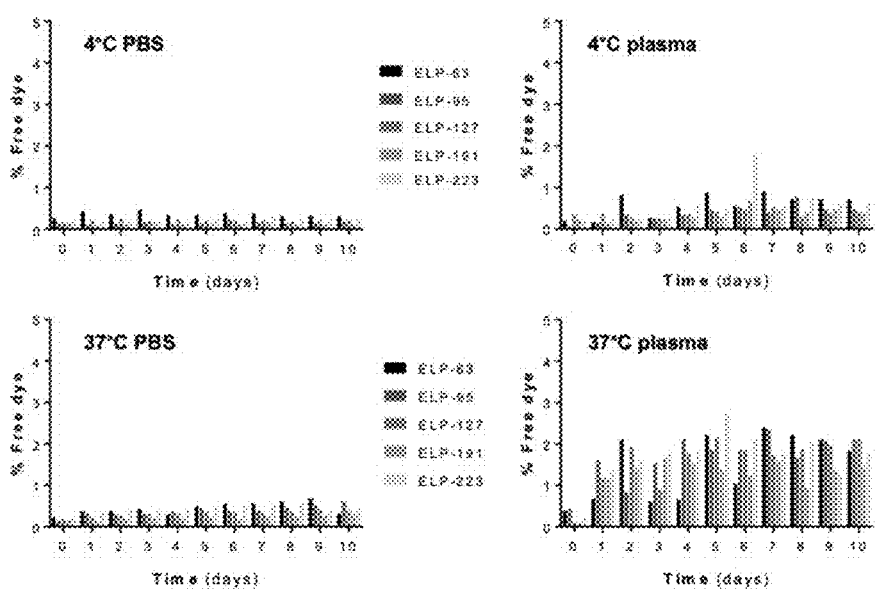

In FIG. 3C, free dye release from the fluorescently-labeled ELP did not exceed 4% in conditions tested, even in the 37° C. plasma samples, as shown by fluorophore loss evaluated using direct fluorescence measurements. These results indicated that even after significant degradation had occurred, the dye was still bound to a protein component.

Example 3

Plasma and Tissue Clearance Pharmacokinetics of ELP Proteins with Varying Molecular Weights A chronic biodistribution study was conducted in SKH1 Elite hairless female mice to determine the effects of MW on plasma pharmacokinetics and total tissue levels of ELP. For pharmacokinetic and biodistribution experiments, five different sized ELPs were selected ranging in MW from 25 to 86 kDa (Table 1).

Animal studies were approved by the Animal Care and Use Committee of the University of Mississippi Medical Center and conducted according to the guidelines of the Guide for the Care and Use of Laboratory Animals. SKH1-Elite hairless female mice (Charles River) were anesthetized with isoflurane (1-3%, to effect), administered carprofen (5 mg/kg subcutaneous), and injected with rhodamine-labeled polypeptides (1.5 µmol/kg) by intravenous injection into the femoral vein. Blood was sampled by tail prick intermittently for 48 hours, collected in Greiner Bio-One MiniCollect capillary blood collection tubes, and plasma was collected after centrifugation.

h, and was directly proportional to MW (Pearson's correlation coefficient r=0.9375, n=5, p=0.0186). The largest protein, ELP-223 (86 kDa), had a terminal half-life of 16.99 h, a 20-fold increase. The distribution half-life was directly proportional to MW (Pearson's correlation coefficient r=0.9929, n=5, p=0.0.0007). Detailed pharmacokinetic analysis of each protein is shown in Table 3. These data demonstrate that the size of the ELP (which can be finely controlled by varying the number of VPGXG (SEQ ID NO: 1) repeats) can be used to tune the plasma half-life. For example, smaller ELPs could be used for drug delivery applications in which fast plasma clearance is desired. Conversely, large ELP carriers could be used to extend the half-life of fused therapeutic agents in therapeutic applications for which a longer plasma and tissue half-life is desired.

TABLE 3

Pharmacokinetics of Different MW ELP Constructs in Mice.

|  |  | ELP-63 (25 kDa) | ELP-95 (37 kDa) | ELP-127 (50 kDa) | ELP-191 (74 kDa) | ELP-223 (86 kDa) |
|---|---|---|---|---|---|---|
| $V_c$ | (L) | 0.004183 | 0.004996 | 0.00442 | 0.004603 | 0.00364 |
| Cl | $\left(\frac{L}{h}\right)$ | 0.00801 | 0.00219 | 0.00105 | 0.00115 | 0.00079 |
| AUC | $\left(\frac{\mu mol \times h}{L}\right)$ | 4.76 | 19.83 | 37.15 | 38.72 | 55.92 |
| $t_{1/2,dist}$ | (h) | 0.07 | 0.77 | 1.07 | 1.97 | 2.27 |
| $t_{1/2,term}$ | (h) | 0.84 | 4.66 | 7.05 | 21.11 | 16.99 |

$V_c$: Central Compartment Volume of Distribution; Cl: Plasma Clearance; AUC: Area Under Curve; $t_{1/2,dist}$: Distribution Half-Life; $t_{1/2,term}$: Terminal Half-Life.

Plasma samples were analyzed for concentration of the polypeptides using quantitative fluorescence analysis. The fluorescence intensity of 2 µl of plasma was measured in a fluorescence plate reader on a NanoQuant Plate (Tecan) using an excitation wavelength of 535 nm and an emission wavelength 585 nm with Magellan software. Fluorescence of the plasma samples was compared to standard curves generated from known concentrations of the injected protein, which allows for comparison of multiple proteins regardless of the fluorescence labeling efficiency of each. A two-compartment model was fitted to the pooled data (mean concentration± SD versus time; n=4 except ELP-127 where n=6) to develop a predictive mathematical model of the plasma concentration versus time.

Whole body fluorescence was measured at the same time as each blood sample by collecting dorsal view images of the live animal using, an IVIS Spectrum. Images were collected using 535-nm excitation and 580-nm emission filters, auto exposure, and small binning. Using Living Image software, regions of interest were drawn over the entire animal, and mean radiant efficiency was measured to determine whole body fluorescence intensity. Standard curves of each injected protein were pipetted into a black 96-well plate, which was subsequently imaged with identical imaging parameters. Mean tissue fluorescence was fit to these standard curves to correct for any differences in labeling levels among polypeptides.

Figure 4A:
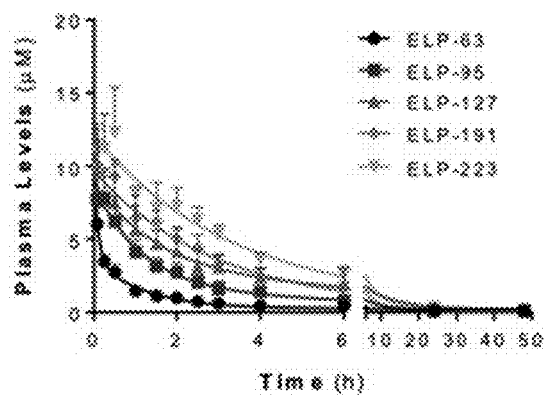
FIGS. 4A-C show graphs illustrating plasma and tissue pharmacokinetics and tissue biodistribution of ELP constructs. (A) Two-compartment pharmacokinetic model of plasma clearance after bolus intravenous injection. (B) Whole-animal fluorescence with time following injection. (C) Tissue accumulation following injection.

After bolus intravenous injection, plasma clearance was fit to a two-compartment pharmacokinetic model (FIG. 4A). This study clearly demonstrated that an increase in MW resulted in slower plasma clearance in vivo. The terminal half-life of the smallest protein, ELP-63 (25 kDa), was 0.84

Figure 4B:
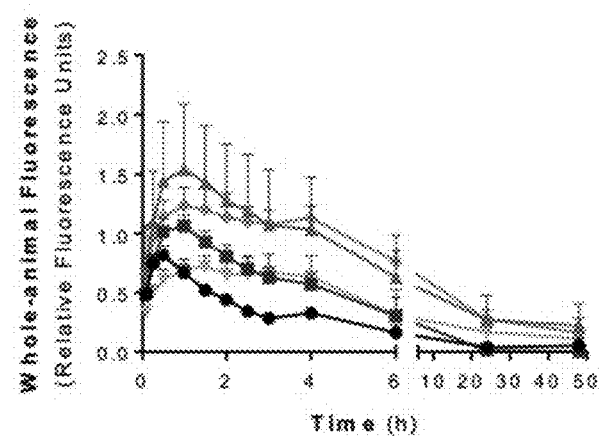

Whole-animal clearance kinetics was determined by non-invasive in vivo imaging of entire mice at each time point. Interestingly, whole-animal fluorescence, depicting tissue levels of fluorescently labeled ELP, increased for the first 30 minutes after injection of the smallest ELP-63, then began to decrease as the protein cleared the body (FIG. 4B). Increasing MW lead to a shift of the tissue clearance curve to the right. ELP-63 peaked at 30 minutes and ELP-223 at 90 min. The ELP proteins with MW above 37 kDa cleared tissue more slowly and were still detectable in the body even 48 h after injection.

An acute biodistribution study was conducted to determine organ levels of ELP proteins with varying MW. The biodistribution of ELP proteins were measured at 4 hours after intravenous injection of fluorescently labeled ELP. Mice were euthanized and major organs removed to quantify ELP tissue levels. Organ biodistribution was assessed with a two-way ANOVA for factors of polypeptide treatment and organ type with post hoc Tukey's multiple comparison. Kidney levels were assessed for differences between treatment groups with a one-way ANOVA with post hoc Tukey's multiple comparison. Correlation was evaluated by Pearson's correlation coefficient. All analyses were done using Prism (GraphPad), and a p value of <0.05 was considered statistically significant.

Figure 4C:
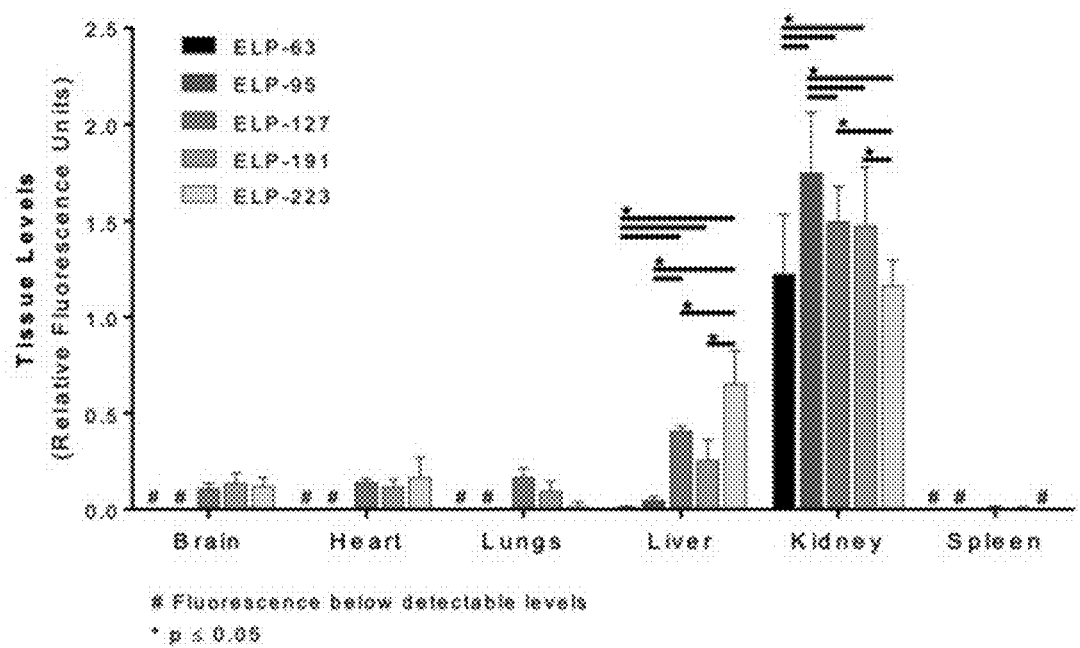

As shown in FIG. 4C, all ELP proteins accumulated most strongly in the kidneys regardless of their MW. The smallest proteins, the 25 kDa ELP-63 and the 37 kDa ELP-95, had either very low or below detectable levels in the brain, heart, lungs, liver and spleen. Statistically significant differences were denoted by * between indicated groups as assessed by a two-way ANOVA with post hoc Tukey's multiple comparison, p<0.05. Polypeptide levels below detectable levels was denoted by #.

The most remarkable finding was the effect of MW on renal deposition of ELP in the kidney. Renal deposition exhibited a non-linear relationship with MW (Pearson's correlation coefficient r=−0.3079, n=5, p=0.6142, $R^2$=0.09481), with the mid-sized proteins accumulating in the kidneys at the highest levels. ELP-63 levels, 1.22 relative fluorescence units (RFU), were significantly lower than ELP-95, 1.75 RFU, ELP-127, 1.49 RFU, and ELP-191 1.47 RFU. ELP-95 levels were additionally higher than ELP-127, ELP-191 and ELP-223 levels. ELP-127 levels were also significantly higher than ELP-223 levels, 1.16 RFU (Two-way ANOVA with post hoc Tukey's multiple comparison, F(4, 90)=8.74, p<0.0001). The liver was the only other organ where all five of the ELP proteins were detected at noteworthy levels (although significantly lower than kidney levels), and liver levels increased with increasing MW.

Example 4

Intrarenal Localization of ELPs

For acute tissue biodistribution studies, SKH1-Elite hairless female mice were anesthetized with isoflurane (1-3%, to effect), administered carprofen (5 mg/kg subcutaneous), and given a single bolus dose of rhodamine-labeled polypeptides (1.5 μmol/kg) by intravenous injection into the femoral vein. Mice were allowed to rouse from anesthesia and move freely in the cage for four hours following injection. They were then re-anesthetized and euthanized while still under anesthesia, and their organs collected for whole organ fluorescence biodistribution analysis (n=4 mice per agent). All major organs were imaged ex vivo using an IVIS Spectrum. Tissues were then embedded in freezing medium (Tissue-Plus O.C.T Compound) and flash frozen. Kidneys were cut into 14 μm sections with a cryostat. Sections were first scanned using a fluorescence slide scanner ScanArray Express (Packard BioScience) using excitation wavelengths 543 nm and emission wavelength 570 nm, scan resolution 50 1. tm, and full scan speed for quantitative scans; and scan resolution 5 μm and half scan speed for high resolution scans. For quantitative scans, the mean fluorescence intensity of tissue sections was analyzed with ImageJ software, and the measured fluorescence intensity was fit to a standard curve of each protein (made from known concentrations of the same labeling batch used for animal injections).

Sections were further analyzed by confocal microscopy. Slides were equilibrated to room temperature and either stained with Hoechst 33342 (5 μg/ml in PBS) or imaged without processing. Stained sections were covered by a coverslip, sealed and imaged immediately by laser scanning confocal microscopy (Nikon C2+) using, 405- and 561-nm lasers for excitation of Hoechst 33342 and rhodamine-labeled protein, respectively. Unprocessed sections were imaged by confocal microscopy image stitching using, 561-nm laser. Brightness levels were adjusted for image quality and don't represent actual intensity.

Figure 5A:
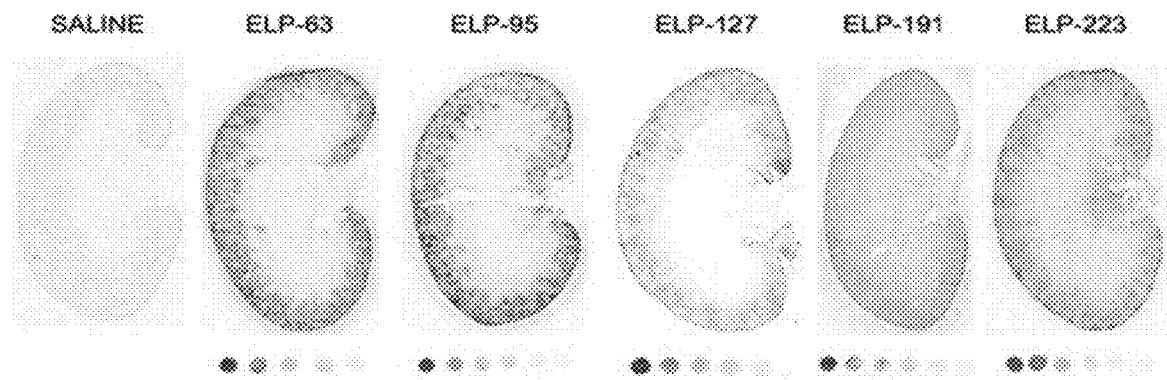
FIGS. 5A-B show an image and a graph illustrating quantitative analysis of ELP intrarenal levels. (A) Quantitative fluorescence histology of kidney sections showing intra-renal concentrations and distribution of ELPs. (B) Accumulation of various ELPs in the renal cortex and renal medulla.

In addition to whole organ ex vivo imaging, quantitative fluorescence histology of kidney sections was performed to accurately measure intra-renal concentrations and to determine the intra-renal distribution. Scans of kidney sections revealed that the smaller ELP-63 and ELP-95 localized were exclusively in the renal cortex (FIG. 5A).

With an increase in MW, the ELP proteins became more distributed in the medulla. Quantitation of these data revealed that the cortical ELP concentration was highest for the smallest proteins, reaching an intra-cortical concentration of around 4 μM at the dose used, and significantly decreasing to around 2 μM for the largest proteins (one-way ANOVA with post hoc Tukey's multiple comparison, F (4, 15)=6.753, p=0.0026; Pearson's correlation coefficient r=−0.8938, n=5, p=0.0409).

Concomitant with the decrease in cortical levels, the medullary ELP levels significantly increased as the polymer size increased (FIG. 5B), from around 0.07 μM for ELP-63 to around 0.84 μM for ELP-223 (one-way ANOVA with post hoc Tukey's multiple comparison, F(4, 15)=5.247, p=0.0076; Pearson's correlation coefficient r=0.7325, n=5, p=0.1593).

Figure 6A:
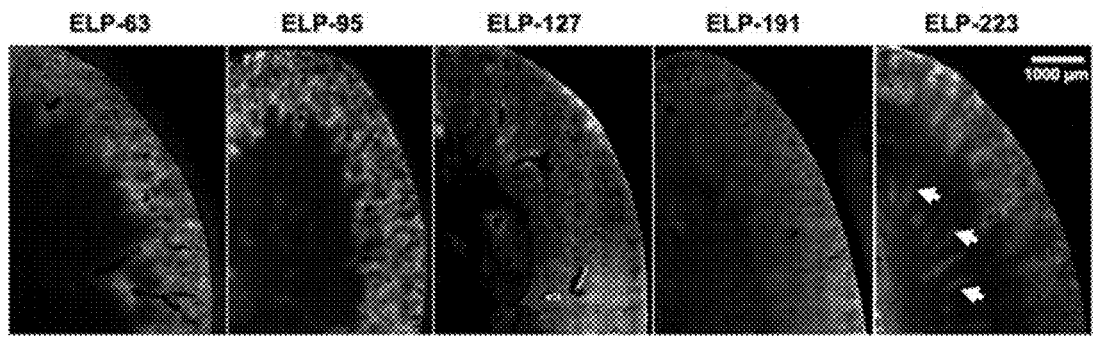
FIGS. 6A-B show images illustrating intrarenal distribution of ELP constructs. (A) Confocal microscopy showing localization of ELPs. (B) Higher magnification imaging with nuclear co-staining showing location of ELP within the renal cortex.
Figure 6B:
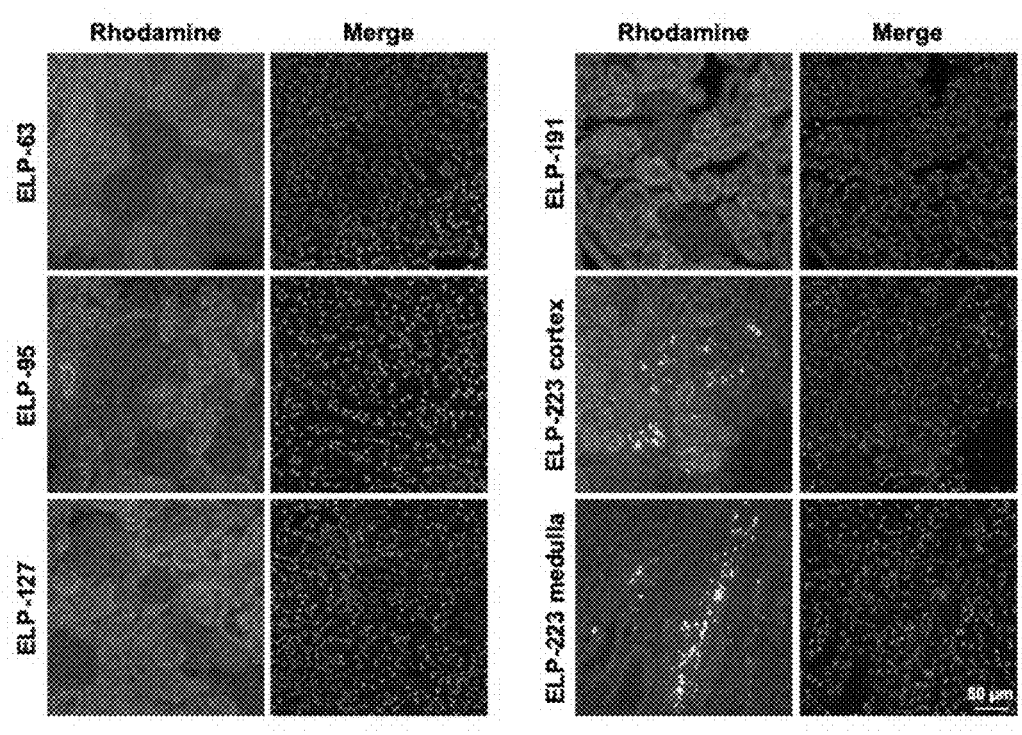

This was confirmed by confocal microscopy of unprocessed slides, shown in FIG. 6A. The smallest ELPs localized cortically and appeared to be mostly present in the renal tubules. As the size increased, the medullary levels increased, and the largest construct, ELP-223, was detectable in distinct medullary structures (FIG. 6A, arrows). Higher magnification imaging with nuclear co-staining revealed that in the cortex, all ELP proteins other than ELP-223 were mostly localized in the tubular epithelial cells, with lower levels in the glomeruli (FIG. 6B). The 86 kDa ELP-223, however, formed aggregates in the glomeruli, and high-resolution images revealed that the distinct medullary signal seen in the slide scanning data was actually protein aggregates in medullary structures (FIG. 6B, right panel middle and bottom).

Figure 5B:
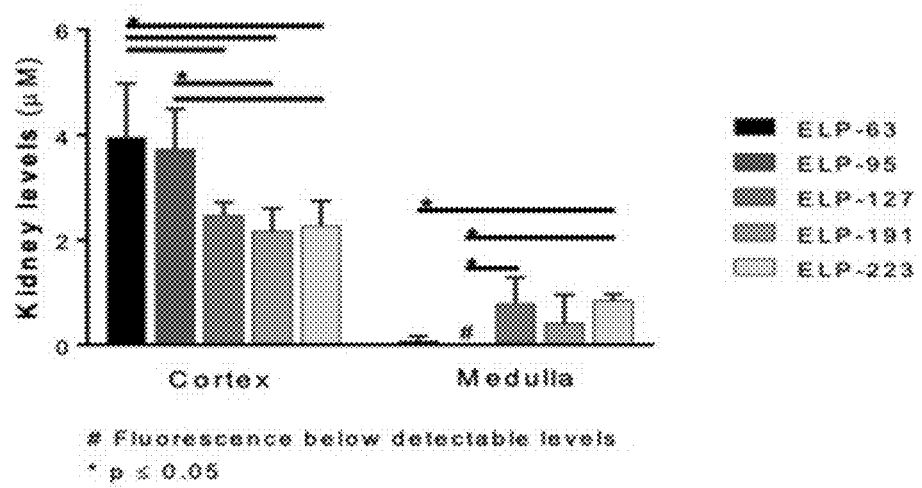

Surprisingly, in addition to differences in organ biodistribution and stability of different size ELP constructs, these results demonstrated that the intra-renal localization of ELP constructs can be targeted exclusively to the cortical region of the kidney if the ELP construct contains about 95 repeat units or less, whose ELP proteins have a MW of 38 kDa or less (FIG. 5B). While in contrast, those ELP constructs containing greater than about 95 repeat units, whose ELP proteins have a MW of 38 kDa or more, showed a renal localization in both the cortical and medullary regions. Further, these data found the amount of ELP protein shifted from cortex to medulla as the size of ELP increased above 38 kDa.

The differential localization of the different size ELP open new strategies in the targeting of therapeutic delivery of biological or chemically based molecules used for the treatment of diseases having distinct disorder profiles, such as renovascular disease or cancer present in the kidney.

Starting with ELP, it was coupled to the therapeutic agent that may be a peptide or protein or protein fragment or nucleic acid or small molecule drug known to have therapeutic activity in renal vascular diseases or cancer. In addition to altering the physical properties of the ELP carrier itself, other attributes of the ELP coupled therapeutic agent are designed. To further optimize the drug delivery to the kidney, in vivo targeting was accomplished by the inclusion of targeting sequences or peptides on the ELP carrier coupled to the targeting agent. The targeting agent may be a peptide, protein, antibody, aptamer, or small molecule with a specific molecular target in the kidney. Further, it also may also contain a cell penetrating peptide, other peptide, or protein capable of penetrating the cellular membrane.

Other modifications of the drug delivery system included a drug binding domain to allow attachment of known or new small molecule therapeutic agents to improve their delivery to treat renal disorders. The drug binding domain may be attached to the ELP carrier via a drug release domain to allow for selective release of the drug under particular environmental conditions or at specific sites within the body. In other delivery vehicles, the ELP coupled therapeutic system includes multiple copies of the therapeutic agent and/or drug binding domain to increase the amount of drug delivered. This may also include the use of 2 or more different therapeutic agents or different drugs attached to the drug binding domain(s) to achieve combination therapy. Other cases may include both a therapeutic agent(s) and a drug binding domain(s) to achieve simultaneous delivery of peptide/protein-based therapeutic agents with small molecule drugs.

All publications, patents, and patent applications mentioned in this specification are herein incorporated by reference to the same extent as if each individual publication, patent, or patent application was specifically and individually indicated to be incorporated by reference.

What is claimed is:

1. A method of treating a renal disorder, the method comprising:
   administering an elastin-like peptide (ELP) and a therapeutic drug to a subject in need thereof;
   wherein the ELP includes at least 5 and up to 671 repeat units having the sequence VPGXG (SEQ ID NO: 1); and wherein X in each of the repeat units is individually selected from the group consisting of any amino acid except proline.

2. The method of claim 1, wherein the ELP includes up to 95 of the repeat units.

3. The method of claim 1, wherein the ELP includes at least 95 of the repeat units.

4. The method of claim 2, wherein the ELP comprises between 5 and 95 of the repeat units.

5. The method of claim 2, wherein the ELP comprises between 31 and 95 of the repeat units.

6. The method of claim 2, wherein the ELP comprises between 63 and 95 of the repeat units.

7. The method of claim 2, wherein the ELP comprises a molecular weight of up to 38 kDa.

8. The method of claim 2, wherein the ELP comprises a molecular weight of between 13 kDa and 38 kDa.

9. The method of claim 2, wherein the repeat units include V:G:A in a 1:4:3 ratio.

10. The method of claim 2, wherein the ELP further comprises one or more of a therapeutic agent or agents, a drug binding domain, a targeting domain, or a cell penetrating peptide.

11. The method of claim 2, wherein the ELP targets the renal cortex.

12. The method of claim 3, wherein the ELP comprises between 95 and 671 of the repeat units.

13. The method of claim 3, wherein the ELP comprises between 95 and 450 of the repeat units.

14. The method of claim 3, wherein the ELP comprises between 95 and 287 of the repeat units.

15. The method of claim 3, wherein the ELP comprises a molecular weight of at least 38 kDa.

16. The method of claim 3, wherein the ELP comprises a molecular weight of between 38 kDa and 257 kDa.

17. The method of claim 3, wherein the repeat units include V:G:A in a 1:4:3 ratio.

18. The method of claim 3, wherein the ELP further comprises one or more of a therapeutic agent or agents, a drug binding domain, a targeting domain, or a cell penetrating peptide.

19. The method of claim 3, wherein the ELP targets the renal medulla and cortex.

20. The method of claim 3, wherein the renal disorder comprises renovascular disease or renal cancer.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial
<220> FEATURE:
<223> OTHER INFORMATION: Synthetic ELP repeat unit
<220> FEATURE:
<221> NAME/KEY: VARIANT
<222> LOCATION: (4)..(4)
<223> OTHER INFORMATION: X is any amino acid except proline

<400> SEQUENCE: 1

Val Pro Gly Xaa Gly
1               5

<210> SEQ ID NO 2
<211> LENGTH: 15
<212> TYPE: PRT
<213> ORGANISM: Artificial
<220> FEATURE:
<223> OTHER INFORMATION: Synthetic ELP
<220> FEATURE:
<221> NAME/KEY: REPEAT
<222> LOCATION: (6)..(10)
<223> OTHER INFORMATION: Between 31 and 671 repeats
<220> FEATURE:
<221> NAME/KEY: VARIANT
<222> LOCATION: (9)..(9)
<223> OTHER INFORMATION: X is individually selected from any amino acid
      except proline in each repeat

<400> SEQUENCE: 2

Met Cys Gly Pro Gly Val Pro Gly Xaa Gly Trp Pro Gly Ser Gly
1               5                   10                  15
```